United States Patent [19]

Van Vlijmen

[11] Patent Number: 5,268,953
[45] Date of Patent: Dec. 7, 1993

[54] X-RAY ANALYSIS APPARATUS INCLUDING GONIOMETER WITH ANGLE ENCODERS

[75] Inventor: Stefan L. A. Van Vlijmen, Almelo, Netherlands

[73] Assignee: U.S. Philips Corporation, New York, N.Y.

[21] Appl. No.: 929,066

[22] Filed: Aug. 12, 1992

[30] Foreign Application Priority Data

Aug. 14, 1991 [EP] European Pat. Off. ........ 91202092.2

[51] Int. Cl.⁵ .......................................... G01N 23/20
[52] U.S. Cl. ....................................... 378/79; 378/73; 378/81
[58] Field of Search ....................... 378/73, 79, 81, 208

[56] References Cited

U.S. PATENT DOCUMENTS

| 3,736,426 | 5/1973 | Anderson et al. | 378/81 |
| 4,535,469 | 8/1985 | Brandt | 378/81 |
| 4,726,047 | 2/1988 | Brouwer et al. | 378/81 |

Primary Examiner—David P. Porta
Attorney, Agent, or Firm—Jack D. Slobod

[57] ABSTRACT

An X-ray analysis apparatus includes angle encoders for the determination of angular positions of at least two rotary shafts, for example the θ shaft for a specimen holder, the 2θ shaft of an X-ray detector arm or the rotary shaft of an X-ray source. Because the angles are directly or indirectly measured relative to a fixed point, preferably coupled to a goniometer frame of the apparatus, accurate angle detection is ensured. The encoders can also be used as adjusting mechanisms for exact, flexible angular adjustment.

15 Claims, 1 Drawing Sheet

X-RAY ANALYSIS APPARATUS INCLUDING GONIOMETER WITH ANGLE ENCODERS

BACKGROUND OF THE INVENTION

1. Field of the Invention

The invention relates to an X-ray analysis apparatus, comprising an X-ray source, an X-ray detector and a specimen holder, and also comprising a goniometer which includes a system of rotary shafts for angular adjustment of the X-ray source and the X-ray detector relative to a specimen to be analysed.

2. Description of the Related Art

An X-ray analysis apparatus of this kind is known from U.S. Pat. No. 4,535,469 where it comprises a goniometer provided with a system of rotary shafts for rotation of a specimen relative to an incident X-ray beam ($\theta$) and for coaxial rotation of a detector arm ($2\theta$) for detection of a (diffracted) X-ray beam to be emitted by the specimen. To this end, such a goniometer comprises, for example a stepping motor and an angle transfer mechanism, or several stepping motors for mutually independent angular adjustment.

A goniometer must provide optimum effective detection of diffracted X-rays, for which exact knowledge of the angle is the variable determining the resolution of the apparatus. An X-ray analysis apparatus comprising such a mechanism has a complex and hence comparatively expensive construction and exhibits, inter alia because of the mechanical transmissions, a rather rigid angular adjustment and ratio of angles, notably also because it is necessary to reduce the lost motion in the rotations. This holds for apparatus comprising a specimen rotary shaft for $\theta$ adjustment in combination with a detection rotary shaft for $2\theta$ adjustment, as well as for apparatus with a stationary specimen and rotary shafts for the X-ray source and the detector.

It is an object of the invention to provide an X-ray analysis apparatus in which exact but flexible angle detection and/or angular adjustment is possible and in which the occurrence of disturbing lost motion is avoided. To achieve this, an X-ray analysis apparatus of the kind set forth is characterized in that at least two shafts of the system of rotary shafts are provided with angle encoders for direct or indirect angle detection.

Because in an apparatus in accordance with the invention angle encoders are arranged between rotary shafts and, for example a frame of the goniometer, any desired angles can be exactly detected or adjusted, exact but flexibly adjustable coupling between angular motions is feasible, and angle detection can be simply performed on-line.

In a preferred embodiment, two rotary shafts are provided with an encoder disc, a read head which is mounted on the same stationary frame being associated with each encoder disc. As a result, the absolute value of the two angles is independently, directly determined and measurable and adjustable as such. The difference between the angles of the two shafts can be calculated from the two angular positions given. Such a construction is attractive, for example for X-ray diffraction apparatus comprising a specimen rotary shaft and a detector rotary shaft which are adjustable in the known $\theta - 2\theta$ geometry.

In a further preferred embodiment, a first shaft comprises an encoder which can be read relative to a stationary frame, a second rotary shafts being readable relative to the first rotary shaft. Using this construction, the angular position of the first rotary shaft as well as the difference between the angles of the two rotary shafts can be directly determined. The angular position of the second rotary shaft relative to a fixed position can be calculated, if desired, from said two values. Such a construction is attractive, for example for X-ray diffraction apparatus comprising a detector rotary shaft for adjustment of irradiation and detection angles relative to a stationary specimen. Preferably, the detector rotation is measured directly relative to a fixed position, because it is predominant for the accuracy of the measurement results.

In a further preferred embodiment, notably for X-ray diffraction apparatus, the encoders have defined measurement positions which can be accessed in accordance with the desired encoder accuracy during read out. In order to access a zero position, notably a microswitch is used for each of the encoders.

An encoder disc, which may be of an arbitrary type, is preferably arranged on a rotary disc mounted on a rotary shaft. Such an encoder disc should exactly indicate the shaft rotation and will, therefore, be selected in respect of exact working, finishing, coefficient of expansion and the like. Measurement through the disc is possible when an encoder disc is constructed so as to be optically transparent. For X-ray analysis apparatus, an encoder disc has a diameter of, for example 15 cm and is provided with, for example 720 lines, so one line per 0.5°; using appropriate known read heads, measurement can be performed with an angular accuracy of up to $10^{-4}$ degrees. The measurement accuracy of the encoders, the construction thereof and the positioning of the read heads relative to a fixed point or to rotary shafts, and the definition of a zero position can be completely adapted to the relevant apparatus requirements. For example, for diffraction apparatus an exactly defined and exactly accessible zero position will be of greater importance to the measurement accuracy than for spectrometry apparatus where a standard specimen can be used.

A substantial advantage of the use of encoders in accordance with the invention is that the dynamic range of the angular motions can be simply adapted. For example, a slow approach and departure from an angular path can be simply realised, this preventing vibrations in the apparatus. Moreover, a desired sub-path, for example a peak searched in a spectrum, can be measured at any desired speed, and so forth.

The accuracy of the angular determination can be further enhanced by association of a plurality of read heads with the encoder disc, for example, two or three heads.

BRIEF DESCRIPTION OF THE DRAWING

Some preferred embodiments in accordance with the invention will be described in detail hereinafter with reference to the drawing. Therein.

DETAILED DESCRIPTION OF THE PREFERRED EMBODIMENTS

Figure 1:
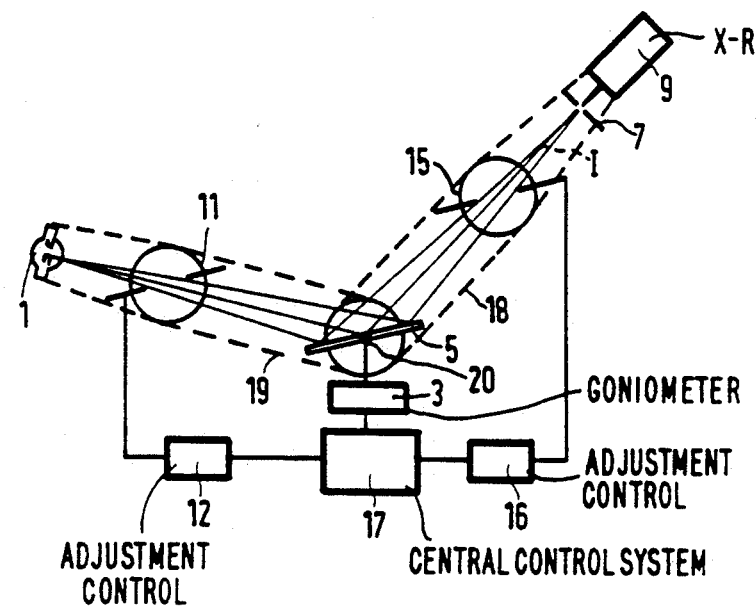
FIG. 1 shows diagrammatically an X-ray analysis apparatus in accordance with the invention.

An X-ray analysis apparatus as shown in FIG. 1 comprises an X-ray source and an entrance slit 11, mounted together on an X-ray source arm 19, and also comprises a goniometer 3, a specimen holder 5, and an X-ray detector 9 which in this case comprises a detector slit 7 and an adjustable scattered radiation diaphragm 15, all of which are mounted on a detection arm 18. Via adjustment controls 12 and 16, the adjustable radiation slits are controllable in a coupled or non-coupled fashion by a central control system 17. The goniometer comprises a goniometer shaft axis 20 which is oriented transversely of the plane of drawing in the Figure and about which the specimen holder 5 and the detector arm 18 are rotatable.

Figure 2:
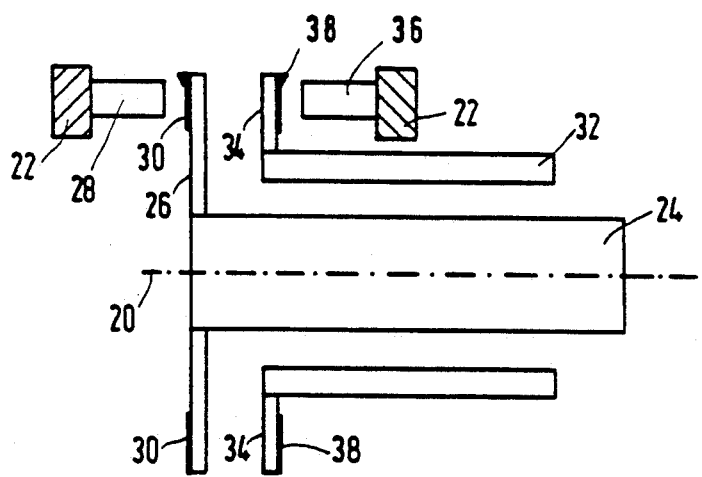
FIG. 2 shows an appropriate angle encoder system comprising two encoders coupled to a fixed points.
Figure 3:
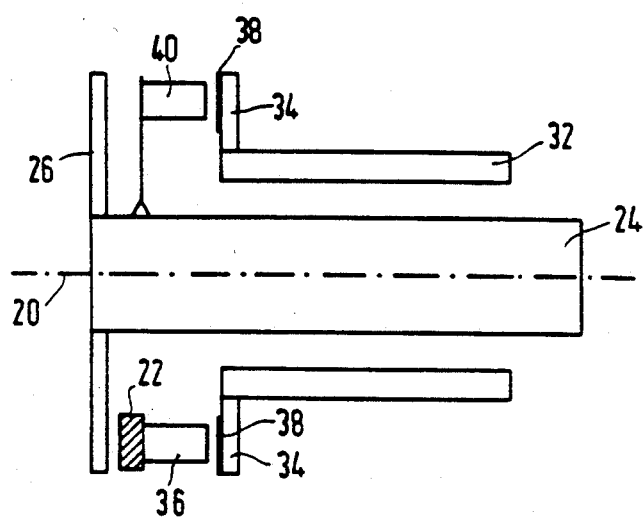
FIG. 3 shows an appropriate angle encoder system comprising two encoders which are coupled to one another, one encoder thereof also being coupled to a fixed point.

In the FIGS. 2 and 3, the shaft axis 20 is shown in the plane of drawing for the sake of clarity.

These Figures also show parts of a support 22 for the goniometer 3. This support forms part of the frame of the X-ray analysis apparatus and in this case acts as the fixed point previously mentioned. All parts of the support 22 form part of a rigid assembly so that they define the same fixed position.

In FIGS. 2 a first rotary shaft 24 with a disc 26 is arranged to be rotable around the axis 20, an encoder disc 30 which can be read by way of a read head 28 which is connected to a fixed point being mounted thereon. A second rotary shaft 32 is arranged so as to be coaxial with the rotary shaft 24, on a disc 34 mounted on said second shaft there is provided which an encoder disc 38 which can be read by a second read head 36 which is also connected to a fixed point. Measurement signals from the two measurement heads can be picked up and processed in a customary manner, so that an exact angular position of each of the shafts 24 and 32 is known on-line and also, if desired, a difference between the angles of the two shafts.

FIG. 3 shows the same shafts 24 and 32 with respective discs 26 and 34. For angular measurement of the shaft 32, a read head 36 which is connected to a fixed point is again arranged opposite the encoder disc 38 provided on disc 34. For angular measurement on the rotary shaft 24, a read head 40 is mounted opposite the encoder disc 38. An angular position of the shaft 32 per se as well as an angular position of the shaft 24 relative to the shaft 32 can thus be directly detected and, if desired, an angular position of the shaft 24 relative to a fixed point can be calculated. Although potentially less practical the discs or any disc can also be fixed to the housing of the apparatus, cooperating read heads then being mounted on the shafts.

Like the detection of angular positions of the various shafts, angular adjustment can also be performed by means of the encoders described. The central control device can then apply, for example digitally, a desired position, from a fixed zero position to the read heads which then act as control heads.

I claim:

1. An X-ray analysis apparatus, comprising an X-ray source, an X-ray detector, a specimen holder, a goniometer which includes a system of at least two coaxial rotary shafts for angular adjustment of the X-ray source and the X-ray detector relative to the specimen holder, and angle encoder means, including two read heads, for detection of angular positions of said two shafts.

2. An X-ray analysis apparatus as claimed in claim 1, wherein the angle encoder means comprises two encoder discs which are mounted on the respective two shafts, said two read heads being coupled to a fixed point and being associated with the two encoder discs, respectively.

3. An X-ray analysis apparatus as claimed in claim 1, wherein the two shafts whose angular positions are detected by said detector means are a specimen shaft about which the specimen holder is angularly adjustable and a detector arm shaft about which the X-ray detector is angularly adjustable.

4. An X-ray analysis apparatus as claimed in claim 1, wherein the angle encoder means comprises an encoder disc which is mounted on one of said two shafts, one of said read heads being coupled to a fixed point and being associated with the encoder disc, and the other of said read heads being coupled to the other of said two shafts and also being associated with the encoder disc.

5. An X-ray analysis apparatus as claimed in claim 1, wherein the two shafts whose angular positions are detected by said detector means are a detector arm shaft about which the X-ray detector is angularly adjustable and an X-ray source arm shaft about which the X-ray source is angularly adjustable.

6. An X-ray analysis apparatus as claimed in claim 4, wherein the shaft on which said encoder disc is mounted is a detector arm shaft about which the X-ray detector is angularly adjustable.

7. An x-ray analysis apparatus as claimed in claim 2, wherein the two encoder discs each have a diameter of approximately 15 cm and are provided with 720 lines, said two read heads performing measurements with a line interpolation up to at least $10^{-3}$.

8. An X-ray analysis apparatus as claimed in claim 1, wherein the encoder means comprises zero position references for said two shafts which are accessible with an accuracy adapted to an encoder measurement accuracy.

9. An X-ray analysis apparatus as claimed in claim 2, wherein the encoder discs are arranged on transparent supports for measurement by the read heads through the supports.

10. An X-ray apparatus as claimed in claim 1, wherein the encoder means can be driven so as to achieve a variable speed of rotation.

11. An X-ray analysis apparatus as claimed in claim 1, wherein the angle encoder means further comprises an encoder disc mounted on one of said two shafts and associated with said two read heads.

12. An X-ray analysis apparatus as claimed in claim 2, wherein the two shafts whose angular positions are detected by said detector means are a specimen shaft about which the specimen holder is angularly adjustable and a detector arm shaft about which the X-ray detector is angularly adjustable.

13. An X-ray analysis apparatus as claimed in claim 4, wherein the two shafts whose angular positions are detected by said detector means are a specimen shaft about which the specimen holder is angularly adjustable and a detector arm shaft about which the X-ray detector is angularly adjustable.

14. An X-ray analysis apparatus as claimed in claim 2, wherein the two shafts whose angular positions are detected by said detector means are a detector arm shaft about which the X-ray detector is angularly adjustable and an X-ray source arm shaft about which the X-ray source is angularly adjustable.

15. An X-ray analysis apparatus as claimed in claim 4, wherein the two shafts whose angular positions are detected by said detector means are a detector arm shaft about which the X-ray detector is angularly adjustable and an X-ray source arm shaft about which the X-ray source is angularly adjustable.

* * * * *